United States Patent
Inoue et al.

(10) Patent No.: US 9,753,492 B2
(45) Date of Patent: Sep. 5, 2017

(54) WRIST-WORN INPUT DEVICE

(71) Applicant: Panasonic Intellectual Property Management Co., Ltd., Osaka (JP)

(72) Inventors: Tsuyoshi Inoue, Nara (JP); Jun Ozawa, Nara (JP); Hiroyuki Motoyama, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 119 days.

(21) Appl. No.: 14/806,850

(22) Filed: Jul. 23, 2015

(65) Prior Publication Data
US 2016/0041580 A1 Feb. 11, 2016

(30) Foreign Application Priority Data

Aug. 6, 2014 (JP) .................................. 2014-160832
Apr. 1, 2015 (JP) .................................. 2015-075296

(51) Int. Cl.
*G06F 1/16* (2006.01)
*A61B 5/0488* (2006.01)
(Continued)

(52) U.S. Cl.
CPC .......... *G06F 1/163* (2013.01); *A61B 5/04002* (2013.01); *A61B 5/0488* (2013.01);
(Continued)

(58) Field of Classification Search
CPC ........ G06F 1/163; G06F 3/017; G06F 3/0412; A61B 5/04002; A61B 5/0488; A61B 5/681
See application file for complete search history.

(56) References Cited

U.S. PATENT DOCUMENTS 4,895,163 A * 1/1990 Libke ................... A61B 5/0537
600/382
2003/0126755 A1* 7/2003 McGorry ............. A61B 5/1071
33/512
(Continued)

FOREIGN PATENT DOCUMENTS

JP 7-248873 9/1995
JP 2000-138858 5/2000

OTHER PUBLICATIONS

Makino, Yasutoshi, et. al.; Comfortable Wristband Interface Measuring Myoelectric Pattern; Second Joint EuroHaptics Conference and Symposium on Haptic Interfaces for Virtual Environment and Teleoperator Systems—Mar. 22-24, 2007.*
(Continued)

*Primary Examiner* — Nicholas Lee
*Assistant Examiner* — Gerald Oliver
(74) *Attorney, Agent, or Firm* — Wenderoth, Lind & Ponack, L.L.P.

(57) ABSTRACT

A wrist-worn input device measuring a biopotential for use in gesture inputting, includes a band that forms at least part of a tubular structure having a first opening and a second opening at the two ends thereof in an axial direction thereof, an electrode open to an internal surface of the band, a position determination unit disposed close to the first opening and having a shape to be engaged with at least part of a periphery of the styloid process of ulna of a user, a biopotential measurement unit that measures the biopotential of the user using the electrode, and a measured potential transmitter that outputs the biopotential of the user.

16 Claims, 18 Drawing Sheets

(51) Int. Cl.
*A61B 5/00* (2006.01)
*G06F 3/01* (2006.01)
*G06F 3/041* (2006.01)
*A61B 5/04* (2006.01)

(52) U.S. Cl.
CPC .............. *A61B 5/681* (2013.01); *G06F 3/017* (2013.01); *G06F 3/0412* (2013.01)

(56) References Cited

U.S. PATENT DOCUMENTS

| | | | | |
|---|---|---|---|---|
| 2006/0028429 A1* | 2/2006 | Kanevsky | ............... | G06F 3/017 345/156 |
| 2009/0326406 A1* | 12/2009 | Tan | .......... | G06F 3/015 600/546 |
| 2012/0127070 A1* | 5/2012 | Ryoo | ...................... | G06F 3/014 345/156 |
| 2013/0265229 A1* | 10/2013 | Forutanpour | ........... | G06F 3/014 345/158 |
| 2014/0240223 A1* | 8/2014 | Lake | ...................... | G08C 17/02 345/156 |

OTHER PUBLICATIONS

Tetsuji Fujiwara, "A Manual of Electromyography and Evoked Potentials" Kinpodo, Jul. 2004, p. 40 (Partial Translation).

* cited by examiner

FIG. 8

| GESTURE | | OPERATION OF CONTROL TARGET DEVICE |
|---|---|---|
| a | ✊ | POWER ON |
| b | ✋ | POWER OFF |
| c | 🖐 | MUTE |
| ... | | |

WRIST-WORN INPUT DEVICE

BACKGROUND

1. Technical Field

The present disclosure relates to a wrist-worn input device that measures a biopotential (such as a myopotential) for use in inputting a gesture.

2. Description of the Related Art

Japanese Unexamined Patent Application Publication Nos. 2000-138858 and 7-248873 disclose a system or an apparatus that is worn around the wrist of a user. The system or apparatus determines the movement of a finger or a hand of a user by measuring a biopotential to control a device. Reference is also made to Tetsuji FUJIWARA, "*Electromyogram and Evoked Potential Manual*" Kinpodo, July 2004, p. 40.

According to Japanese Unexamined Patent Application Publication Nos. 2000-138858 and 7-248873, electrodes are disposed on a belt-like band, something like the band of a watch. With the electrodes in contact with the skin of the user, myopotential is measured when the user moves his or her finger or hand. The movement of the finger or hand of the user is thus determined by comparing the measured myopotential with criteria data.

The myopotential generated when the user moves the finger or hand is different depending a position where measurement is made. In order to precisely measure the myopotential using the same criteria data, a contact position of each electrode is stabilized.

SUMMARY

One non-limiting and exemplary embodiment provides a wrist-worn input device that stabilizes a contact position of electrodes in a state worn around the wrist of a user.

In one general aspect, the techniques disclosed here feature a wrist-worn input device measuring a biopotential for use in inputting a gesture. The wrist-worn input device includes a band that forms at least part of a tubular structure having a first opening and a second opening at two ends thereof in an axial direction thereof, one or more electrodes open to an internal surface of the band, a first position determination unit that is located close to the first opening and has a shape to be engaged with at least part of a periphery of the styloid process of ulna of a user, a measurement unit that measures a biopotential of the user using the one or more electrodes, and an output unit that outputs the biopotential of the user measured by the measurement unit. The one or more electrodes include at least one measurement electrode. At least one measurement electrode is located at a center point between the first opening and the second opening along the axial direction or located at a point closer to the second opening than to the center point along the axial direction.

It should be noted that general or specific embodiments may be implemented as a system, a method, an integrated circuit, a computer program, a computer-readable storage medium, or any selective combination thereof. The computer-readable storage medium may include a non-volatile recording medium, such as a compact disc read-only memory (CD-ROM).

According to the disclosure, the contact position of the electrodes are stabilized when the input device is worn around the wrist of the user.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 illustrates an example of an operation criterion of the embodiment;

DETAILED DESCRIPTION

Figure 1:
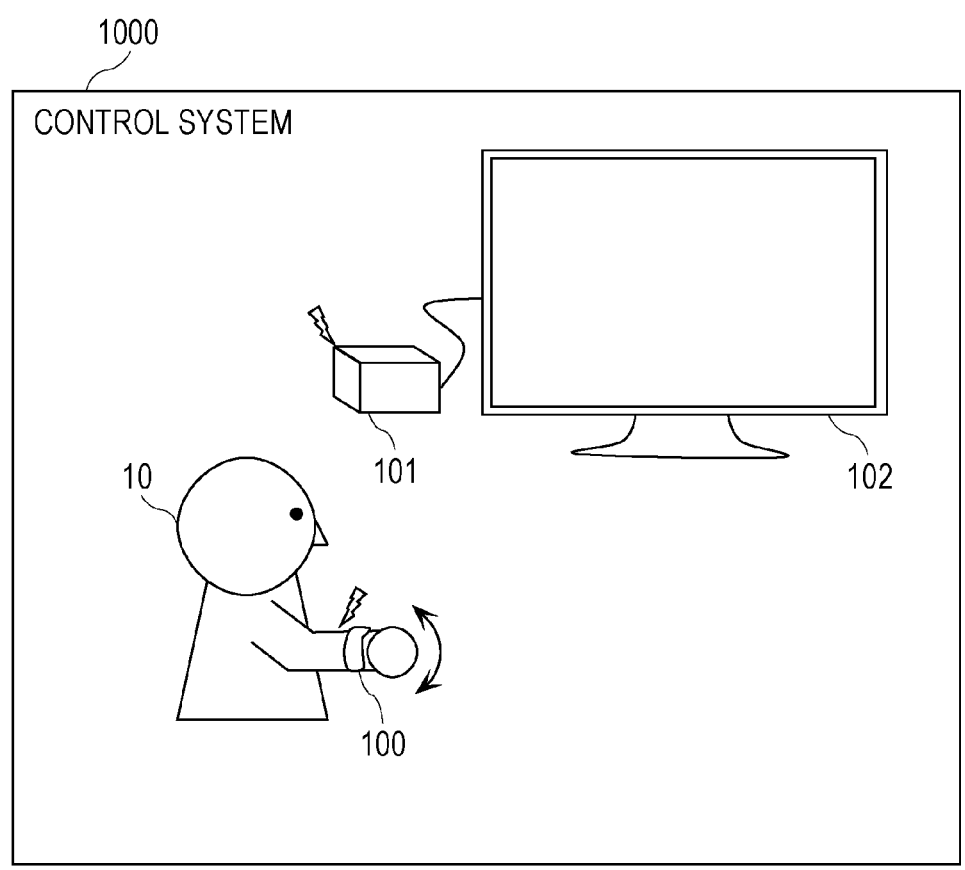
FIG. 1 illustrates how an input device of an embodiment is used.

Underlying Knowledge Forming Basis of the Present Disclosure

A wrist-worn input device of an embodiment of the disclosure measures a biopotential for use in inputting a gesture. The input device includes a band that forms at least part of a tubular structure having a first opening and a second opening at two ends thereof in an axial direction thereof, one or more electrodes open to an internal surface of the band, a first position determination unit that is located close to the first opening and has a shape to be engaged with at least part of a periphery of the styloid process of ulna of a user, a measurement unit that measures the biopotential of the user using the one or more electrodes, and an output unit that outputs the biopotential of the user measured by the measurement unit. The one or more electrodes include at least one measurement electrode. At least one measurement electrode is located at a center point between the first opening and the second opening along the axial direction or located at a point closer to the second opening than to the center point along the axial direction.

In other words, the input device of the embodiment of the disclosure is a wrist-worn type of input device that measures the biopotential for use in inputting a gesture. The input device includes the band to be worn around the wrist of the user, the one or more electrodes open to a first surface that is to be in contact with the wrist of the user, the first position determination unit that is formed in the band and shaped to be engaged with at least part of the periphery of the styloid process of ulna of the user, the measurement unit that measures the biopotential of the user using the one or more electrodes, and the output unit that outputs the biopotential of the user measured by the measurement unit. The position determination unit is formed along a first side extending along the longitudinal direction of the band. The one or more electrodes include at least one measurement electrode. At least one measurement electrode is located at the center point between the first side and a second side opposed to the first side on the first surface of the band, or at the point closer to the second side than to the center point.

In this configuration, the first position determination unit shaped to engage with at least the part of the periphery of the styloid process of ulna of the user is located close to the first opening. The user may thus wear the input device such that the first position determination unit engages with the styloid process of ulna. In other words, the first position determination unit assists the user to wear the input device at an appropriate position. Since the input device is worn with the first position determination unit to be engaged with the styloid process of ulna of the user, a displacement in the location of the input device with respect to the wrist with the input device worn around the wrist (such as a rotation around the wrist) is controlled. The input device, while being worn around the wrist, is thus stabilized in the contact position of the electrodes.

In the configuration, the measurement electrode is located at the center point between the first opening and the second opening along the axial direction or at the point closer to the second opening than to the center point. When the input device is worn around the wrist of the user in a manner such that the first position determination unit engages with the styloid process of ulna of the user, the measurement electrode may be spaced apart from the hand joint of the user. This arrangement controls a displacement in the contact position of the measurement electrode or keeps the measurement electrode from lifting off the skin of the user when the user bends or stretches the hand joint. More specifically, the input device is stabilized in the contact position of the measurement electrode, thereby reliably measuring the biopotential.

The one or more electrodes may include at least one reference electrode. At least one reference electrode may be located in alignment with the first position determination unit along the axial direction and is used to measure a reference potential that is used to normalize the biopotential measured using at least one measurement electrode. The reference electrode and the first position determination unit may be aligned with each other in the axial direction.

In this configuration, the reference electrode and the first position determination unit are aligned with each other in the axial direction. When the input device is worn around the wrist of the user in a manner such that the first position determination unit engages with the styloid process of ulna of the user, the reference electrode is placed on the ulna. In order to measure an action potential from the surface of the body of the user, an electrode serving as a reference is desirably placed on an immobile skin portion, such as the skin on a bone, other than a target muscle. (Reference is made to Reference is also made to Tetsuji FUJIWARA, "*Electromyogram and Evoked Potential Manual*" Kinpodo, July 2004, p. 40). With the reference electrode placed on the ulna, the input device may appropriately normalize the biopotential measured using the measurement electrode.

The one and more electrodes may further include at least one ground electrode. At least one ground electrode may be located in alignment with the first position determination unit along the axial direction.

In this configuration, the ground electrode and the first position determination unit are aligned with each other in the axial direction. When the input device is worn around the wrist of the user in a manner such that the first position determination unit engages with the styloid process of ulna of the user, the ground electrode is placed on the ulna. In order to measure an action potential from the surface of the body of the user, an electrode serving as a reference is desirably placed on an immobile skin portion, such as on the skin on a bone, other than a target muscle. (Reference is made to Reference is also made to Tetsuji FUJIWARA, "*Electromyogram and Evoked Potential Manual*" Kinpodo, July 2004, p. 40). With the ground electrode placed on the ulna, the input device may allow itself to be appropriately grounded.

The first position determination unit may be a cutout formed in an end edge portion of the band at the first opening.

In this configuration, the first position determination unit is formed at the end edge portion of the band at the first opening thereof. The input device is worn such that the cutout is engaged with the periphery of the styloid process of ulna of the user and the contact position of the electrode is thus stabilized.

The first position determination unit may be a recess formed on the internal surface of the band.

In this configuration, the first position determination unit is the recess formed on the internal surface of the band. The input device is worn such that the recess receives the styloid process of ulna of the user and the contact position of the electrode is thus stabilized.

The recess may be a through-hole penetrating through the band, and the first position determination unit may include a cap closing the through-hole on an external surface of the band.

In this configuration, the first position determination unit is the through-hole, and the through-hole is closed with the cap. The input device is worn such that the through-hole receives the styloid process of ulna of the user, and the contact position of the electrode is thus stabilized.

At least part of the cap may be transparent.

In this configuration, at least part of the cap is transparent. The user wears the input device on the user's wrist to cause the styloid process of ulna of the user to be received in the through-hole while watching the styloid process of ulna of the user. The cap is used to assist the user to wear the input device at an appropriate location.

The cap may detachably close the through-hole.

In this configuration, the cap detachably closes the through-hole. When the input device is worn around the wrist, the user opens the cap and causes the styloid process of ulna of the user to be received in the through-hole while watching the styloid process of ulna of the user. The cap thus assists the user to wear the input device at an appropriate location.

The band may include a first band portion and a second band portion lower in flexibility than the first band portion. The first position determination unit may be formed in the first band portion.

In this configuration, the first position determination unit is formed in the first band portion more flexible than the second band portion. The first position determination unit responds flexibly to a difference in the shape of the styloid process of ulna of the user, and fits with the styloid process of ulna of the user.

The wrist-worn input device may further include a second position determination unit that is located closer to the second opening, and has a shape to be engaged with at least part of the periphery of the styloid process of ulna of the user.

In this configuration, the two position determination units respectively correspond to the right wrist and left wrist of the user. The contact position of each electrode is stable regardless of whether the input device is worn around either the right wrist or left wrist.

At least one measurement electrode may be located at the center point.

In this configuration, the input device may include the first position determination unit and the second position determination unit. Regardless of whether the input device is worn around the right wrist or left wrist, the measurement electrode is spaced apart from the hand joint of the user. The contact position of the measurement electrode in the input device is stable enough to allow the biopotential to be measured reliably.

The one or more electrodes may further include a plurality of reference electrodes. Each of the reference electrodes may be used to measure a reference potential that is used to normalize the biopotential measured using at least one measurement electrode. The measurement unit normalizes the biopotential measured using at least one measurement electrode by selectively using one of a plurality of reference potentials measured using the reference electrodes.

In this configuration, one of the reference potentials measured using the reference electrodes is selectively used to normalize the biopotential measured using the measurement electrode. The biopotential is normalized using a more appropriate reference potential.

The wrist-worn input device may further include on an external surface of the tubular structure a display having a width in a lateral direction and a height in a vertical direction. The first position determination unit may be located above the center of the display.

In this configuration, the user may wear the input device around his or her wrist such that the first position determination unit engages with the styloid process of ulna. The input device is thus mounted such that the styloid process of ulna is above the center of the display. In other words, the user is assisted to wear the input device such that the display is aligned correctly.

The wrist-worn input device may further include a display on an external surface of the tubular structure. The display may display a screen in alignment such that the first position determination unit is located above the center of the screen.

In this configuration, when the input device is worn around the wrist of the user such that the first position determination unit engages with the styloid process of ulna, the screen of the display is aligned such that the styloid process of ulna is positioned above the center of the display. More specifically, the screen is presented such that the user may easily view the screen.

According to another aspect of the disclosure, there is provided a wrist-worn input device measuring a biopotential for use in inputting a gesture. The input device includes a band that forms at least part of a tubular structure having a first opening and a second opening at two ends thereof in an axial direction thereof, one or more electrodes open to an internal surface of the band, a first position determination unit that is located close to the first opening and has a shape to be engaged with at least part of a periphery of the styloid process of ulna of a user, a sensor that measures the biopotential of the user using the one or more electrodes, and a communication device that transmits the biopotential of the user measured by the sensor. The one or more electrodes include at least one measurement electrode. At least one measurement electrodes is located at a center point between the first opening and the second opening along the axial direction or located at a point closer to the second opening than to the center point along the axial direction.

According to another aspect of the disclosure, there is provided an wrist-worn input device. The wrist-worn input device includes a band in a rectangular development shape, except a cutout, extending along a first longitudinal line and a second longitudinal line, and having the cutout extending along the first longitudinal line, and a plurality of electrodes including one or more measurement electrodes, one or more reference electrodes, and one or more ground electrodes, each of the electrodes open to an internal surface of the band. A center line extends along the internal surface between the first longitudinal line and the second longitudinal line. The one or more measurement electrodes are located in an area between the center line and the second longitudinal line. One or more potentials measured by using the one or more measurement electrodes are normalized by using one or more potentials measured by the one or more reference electrodes. A longest distance between the cutout and the one or more reference electrodes is shorter than a shortest distance between the cutout and the one or more measurement electrodes, and/or a longest distance between the cutout and the one or more reference electrodes is shorter than a shortest distance between the cutout and the one or more ground electrodes. The one or more reference electrodes and the one or more ground electrodes are located in an area between a line running from a first intersection of the cutout and the first longitudinal line in perpendicular to the second longitudinal line and a line running from a second intersection of the cutout and the first longitudinal line in perpendicular to the second longitudinal line.

Embodiments

With reference to the drawings, embodiments of a control system including a wrist-worn input device is described below.

The embodiments described below are general or specific embodiments of the disclosure. Elements, and numerical values, shapes, and materials of the elements, and mounting locations and connection forms of the elements, steps, and the order of the steps in the embodiments are described for exemplary purposes only, and are not intended to limit the disclosure. Among the elements in the embodiments, elements not described in the independent claims indicative of higher concepts may be described as optional elements. The drawings are diagrammatic and do not necessarily illustrate elements in a strictly precise form.

Use Scene of Control System

Figure 2:
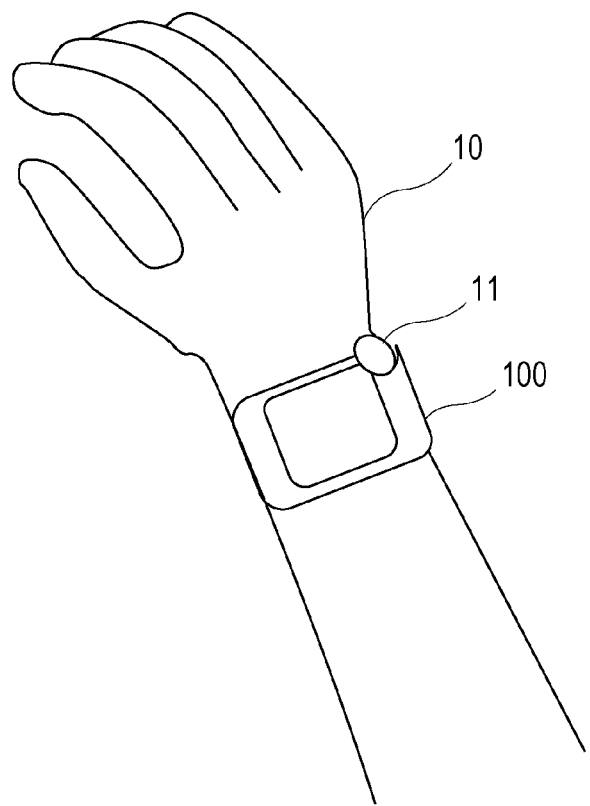
FIG. 2 illustrates the input device of the embodiment that is worn around the wrist of a user.

FIG. 1 illustrates a use scene of a control system 1000 including an input device 100 of an embodiment. FIG. 2 illustrates the input device 100 of the embodiment worn around the wrist of a user 10.

The control system 1000 includes an input device 100, an action determination device 101, and a control target device 102. Referring to FIG. 1, the user 10 of the control system 1000 is illustrated, but the user 10 is not an element of the control system 1000.

As illustrated in FIG. 1 and FIG. 2, the input device 100 is worn around the wrist of the user 10. The styloid process of ulna 11 of the wrist of the user 10 is used as a reference location that serves to stabilize the mounting position of the input device 100. The input device 100 is described in detail below in the process of using the styloid process of ulna 11 as a reference location.

The action determination device 101 determines an action of the user 10 (namely, a gesture of the user 10) corresponding to the biopotential measured by the input device 100 by referencing a pre-stored potential pattern. The action determination device 101 transmits to the control target device 102 an operation instruction responsive to the determined gesture.

The control target device 102 is a display, such as a television receiver. The control target device 102 may also be a digital versatile disk (DVD) player, or a digital video recorder. The control target device 102 may also be a lighting device or a personal computer.

FIG. 1 illustrates a non-portable display as an example of the control target device 102. The control target device 102 may be a device mounted on the user 10. For example, the control target device 102 may be a device worn around the wrist of the user 10 (such as a smart watch). In such a case, the input device 100 and the action determination device 101 may be included in the control target device 102.

Structure of Input Device

The structure of the input device 100 is described in detail.

Figure 3A:
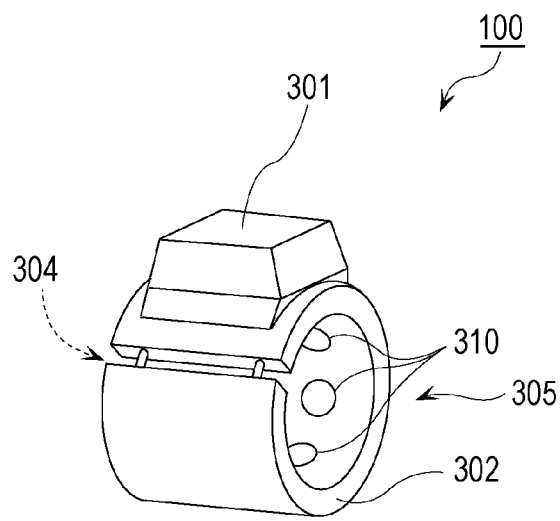
FIG. 3A and FIG. 3B are perspective views of the input device of the embodiment.
Figure 3B:
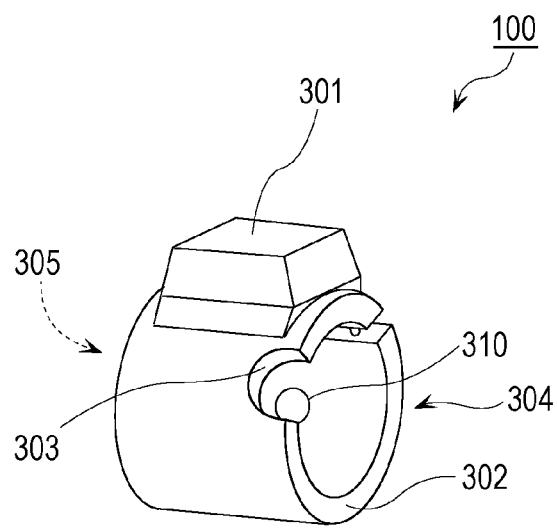

FIG. 3A and FIG. 3B are perspective views of the input device 100 of the embodiment. More specifically, FIG. 3A and FIG. 3B are perspective views of the input device 100 viewed from different directions.

Figure 3C:
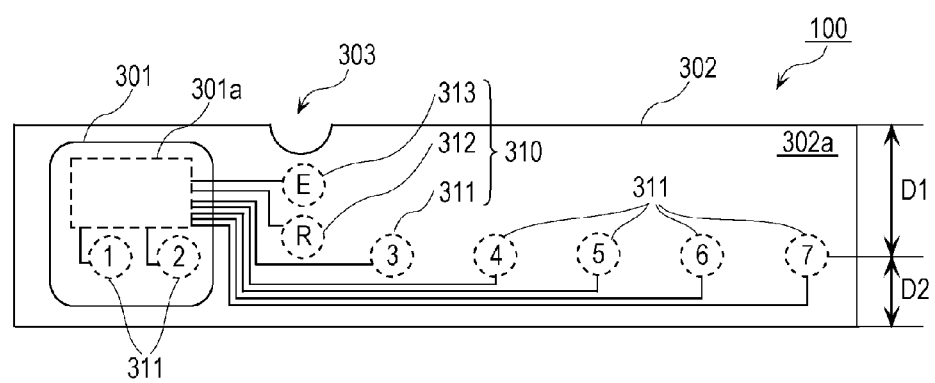
FIG. 3C and FIG. 3D illustrate bands of the input devices of the embodiment in an unfolded state.
Figure 3D:
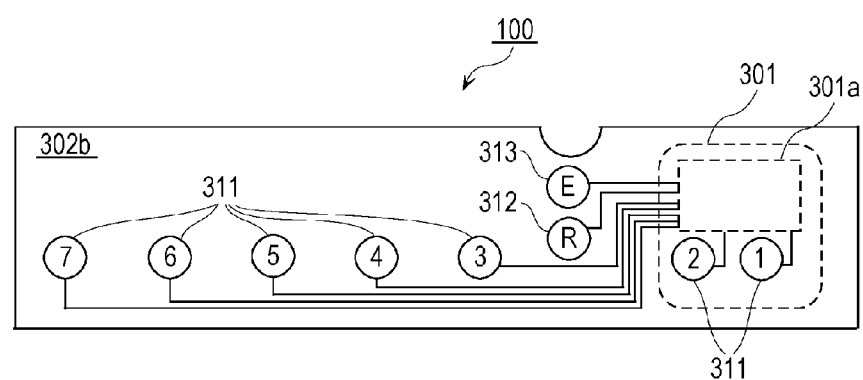

FIG. 3C and FIG. 3D illustrate the input device 100 of the embodiment with a band 302 thereof unfolded. More specifically, FIG. 3C illustrates the input device 100 with the band 302 unfolded and with an external surface 302a (second surface) viewed from the outside. FIG. 3D illustrates the input device 100 with the band 302 unfolded and with an internal surface 302b (first surface) viewed from the inside.

Referring to FIG. 3C and FIG. 3D, invisible portions are represented by broken lines. Electrical wirings electrically connecting elements are represented by solid lines.

Referring to FIG. 3A through FIG. 3D, the input device 100 includes a device body 301, the band 302, a position determination unit 303, and multiple electrodes 310.

The device body 301 houses a variety of devices that cause the input device 100 to work. For example, the device body 301 houses a signal processing circuit, a battery, and a radio communication device, and the like. In the embodiment, the device body 301 houses a circuit board 301a having circuitry to measure the biopotential.

The band 302 is worn around the wrist of the user 10. In other words, the band 302 is a belt-like member that covers partly or wholly around the periphery of the wrist of the user 10. The band 302 forms at least part of a tubular structure having a first opening 304 and a second opening 305 in an axial direction thereof. The band 302 may be a strap or a bracelet manufactured of resin, metal, or fiber.

The device body 301 is arranged on the external surface 302a of the band 302. The external surface 302a is opposed to an internal surface 302b which is configured to be in contact with the wrist of the user 10. More specifically, the external surface 302a is externally exposed with the band 302 worn around the wrist of the user 10 (namely, in a state in which a tubular structure is formed by the band 302). In the embodiment, the device body 301 and the band 302 are integrated in a unitary body.

The position determination unit 303 is located close to a first opening 304, and is shaped to be engaged with at least part of the styloid process of ulna 11 of the user 10. In other words, the position determination unit 303 is located closer to the first opening 304 than to the second opening 305. In the embodiment, the position determination unit 303 is a semi-circular cutout formed along a side (first side) extending in a longitudinal direction of the band 302. More specifically, the position determination unit 303 is a cutout formed on the side of the first opening 304 of the band 302. When the input device 100 is worn around the wrist of the user 10, the position determination unit 303 surrounds the styloid process of ulna 11.

The ulna is a bone forming the forearm of the human. The styloid process of ulna 11 is a process at the distal end of the ulna (the end closer to the hand), and projects from the wrist.

The multiple electrodes 310 are open to the internal surface 302b of the band 302. The multiple electrodes 310 are electrically connected to a circuit board 301a contained in the device body 301 via metal wirings.

The internal surface 302b is configured to be in contact with the wrist of the user 10. More specifically, the internal surface 302b becomes an inner periphery when the band 302 is worn around the wrist of the user 10.

In the embodiment, the multiple electrodes 310 includes seven measurement electrodes 311, a reference electrode 312, and a ground electrode 313.

Each of the measurement electrodes 311 is used to measure the biopotential at a location where each measurement electrode 311 is in contact with the skin.

The reference electrode 312 is used to measure a reference potential that is used to normalize the biopotential measured by the measurement electrode 311. The normalization of the biopotential is to adjust the biopotential according a given rule. More specifically, the biopotential measured using each measurement electrode 311 is adjusted using as a criterion a reference potential measured using the reference electrode 312. In the embodiment, a difference resulting from subtracting the reference potential measured using the reference electrode 312 from the biopotential measured using each measurement electrode 311 is output as a biopotential (measurement results).

The ground electrode 313 is used to ground electronic devices included in the input device 100.

Referring to FIG. 2, the input device 100 is worn around the wrist of the user 10 such that the measurement electrodes 311, the reference electrode 312, and the ground electrode 313 are in contact with the skin of the wrist of the user 10. As a result, the biopotential is measured by the input device 100.

In order to measure an action potential from the surface of the body of the user, an electrode serving as a reference is desirably placed on an immobile skin portion, such as on the skin on a bone, other than a target muscle (Reference is made to Reference is also made to Tetsuji FUJIWARA, "*Electromyogram and Evoked Potential Manual*" Kinpodo, July 2004, p. 40). In the embodiment, the reference electrode 312 and the ground electrode 313 are located in alignment with the position determination unit 303 in a direction intersecting the longitudinal direction of the band 302. More specifically, the reference electrode 312 and the ground electrode 313 are located in alignment with the position determination unit 303 the axial direction of a tubular shape formed by the band 302.

The longitudinal direction is a circular direction of the tubular shape formed by the band 302 when the band 302 is worn around the wrist of the user 10. The direction intersecting the longitudinal direction is substantially perpendicular to the longitudinal direction. More specifically, the direction intersecting the longitudinal direction is the axial direction of the tubular shape formed by the band 302 when the band 302 is worn around the wrist of the user 10, and corresponds to the direction along which the ulna extends.

When the input device 100 is worn around the wrist of the user 10 such that the position determination unit 303 engages with the styloid process of ulna 11, the reference electrode 312 and the ground electrode 313 are placed on the ulna. More specifically, the input device 100 assists the user 10 to wear the input device 100 such that the reference electrode 312 and the ground electrode 313 are placed on the ulna.

Referring to FIG. 3C, the measurement electrodes 311 are located at locations closer to the second opening 305 than to the center location between the first opening 304 and the second opening 305 along the axial direction of the tubular shape. More specifically, the measurement electrodes 311 are spaced more apart from the first side of the band 302 where the position determination unit 303 is formed. The measurement electrodes 311 are exposed at the locations on the internal surface 302*b* of the band 302 closer to the second side opposed to the first side along which the position determination unit 303 is formed. As illustrated in FIG. 3C, a distance D1 between the measurement electrodes 311 and the first side is longer than a distance D2 between the measurement electrodes 311 and the second side.

Functional Configuration of Control System

Figure 4:
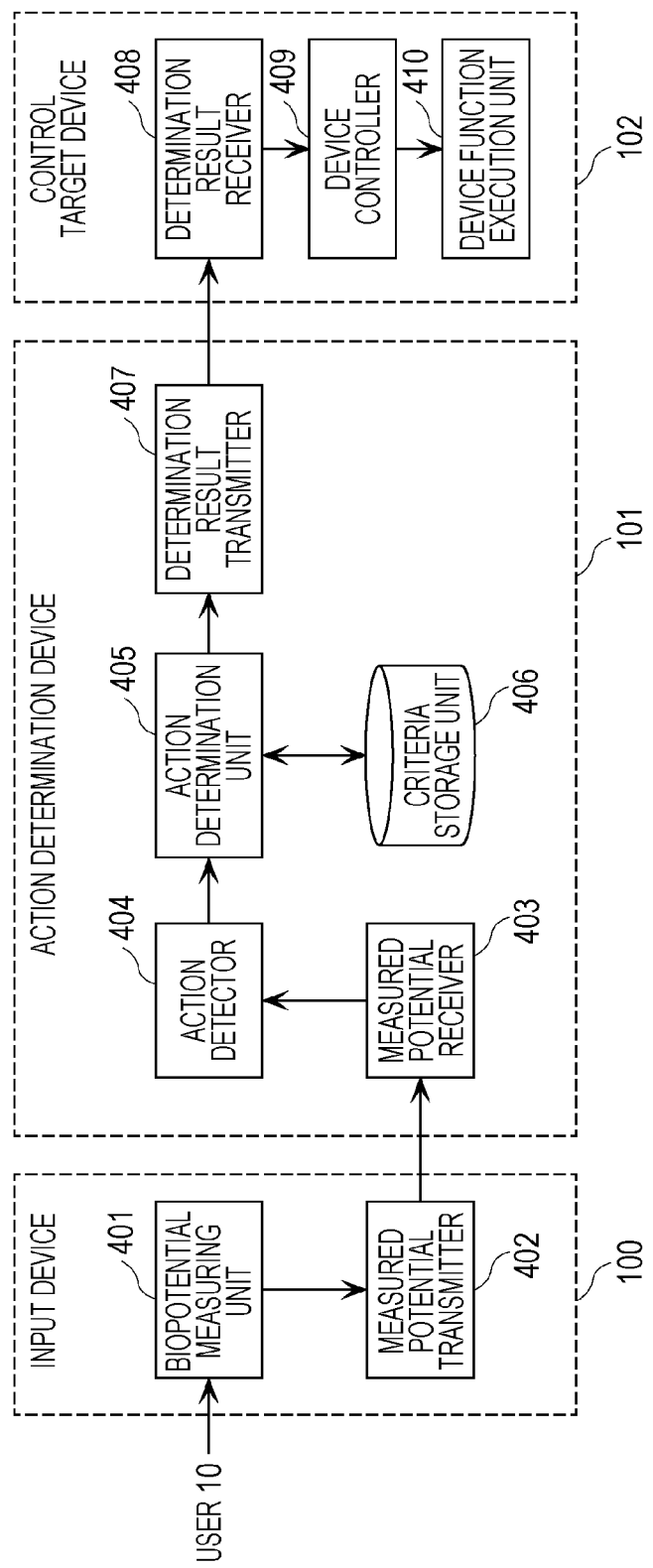
FIG. 4 is a functional block diagram illustrating a control system of the embodiment.

The functional configuration of the control system 1000 is described below. FIG. 4 is a functional block diagram illustrating of the control system 1000 of the embodiment.

The control system 1000 includes the input device 100, the action determination device 101, and the control target device 102. The functional configuration of the input device 100 is described first.

The input device 100 includes a biopotential measuring unit 401 and a measured potential transmitter 402.

The biopotential measuring unit 401 is implemented by a circuit board 301*a*. The biopotential measuring unit 401 measures the biopotential of the user 10 using the multiple electrodes 310. More specifically, the biopotential measuring unit 401 calculates as a biopotential a difference between the potential measured using each of the measurement electrodes 311 and the reference potential measured using the reference electrode 312. Multiple biopotentials thus calculated are referred to as a biopotential set. The biopotential sets are measured in a time sequence.

The measured potential transmitter 402 is an example of an outputter, and implemented by the circuit board 301*a*, an antenna (not illustrated), and the like. The measured potential transmitter 402 outputs the biopotential sets measured by the biopotential measuring unit 401 in the time sequence to the action determination device 101.

The functional configuration of the action determination device 101 is described below. The action determination device 101 includes a measured potential receiver 403, an action detector 404, an action determination unit 405, a criteria storage unit 406, and a determination result transmitter 407.

The measured potential receiver 403 receives the biopotential set from the measured potential transmitter 402, and transfers the biopotential set to the action detector 404.

The action detector 404 references pre-stored detection criteria, and detects the biopotential set measured when the user 10 takes any intentional action (gesture), from among the multiple biopotential sets measured by the biopotential measuring unit 401 in the time sequence.

For example, the action detector 404 stores a predetermined threshold potential as a detection criterion. The action detector 404 detects the biopotential set including the biopotential equal to or above the predetermined threshold potential from among the multiple biopotential sets measured by the biopotential measuring unit 401 in the time sequence. The predetermined threshold potential may be a myopotential corresponding to a predetermined action of the user 10.

The action determination unit 405 references determination criteria stored on the criteria storage unit 406, and determines a gesture corresponding to the biopotential set detected by the action detector 404. More specifically, the action determination unit 405 compares a predetermined concordance rate with a concordance rate between a biopotential pattern responsive to the gesture indicated by the determination criteria and a biopotential pattern detected by the action detector 404. The action determination unit 405 thus determines the gesture corresponding to the detected biopotential set.

The criteria storage unit 406 stores the determination criteria that associates the potential with the action (gesture). An example of the determination criteria is a biopotential pattern that associates magnitudes of multiple myopotentials with gestures. The magnitude of a myopotential may be the absolute value of a myopotential, or the absolute value of a ratio of the myopotential to a predetermined potential.

The determination result transmitter 407 transmits to the control target device 102 information of the gesture determined by the action determination unit 405 (hereinafter referred to as a "gesture").

The functional configuration of the control target device 102 is described below. The control target device 102 includes a determination result receiver 408, a device controller 409, and a device function execution unit 410.

The determination result receiver 408 receives the gesture of the user 10 determined by the action determination unit 405 in the action determination device 101, and transfers the received gesture to the device controller 409. The device controller 409 references the pre-stored operation criteria and determines an operation corresponding to the gesture of the user 10. The device controller 409 executes the determined operation by controlling the device function execution unit 410.

Process of Control System

Figure 5:
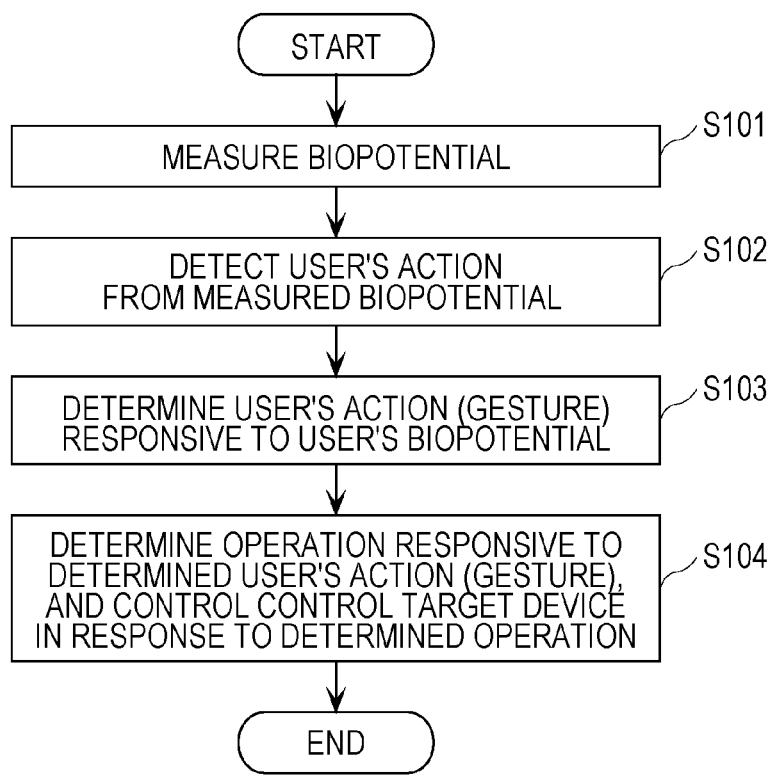
FIG. 5 is a flowchart illustrating a process of the control system of the embodiment.

The process of the control system 1000 thus constructed is described below. FIG. 5 is a flowchart illustrating the process of the control system 1000 of the embodiment. The myopotential is used as the biopotential in the process.

Step S101

Figure 6:
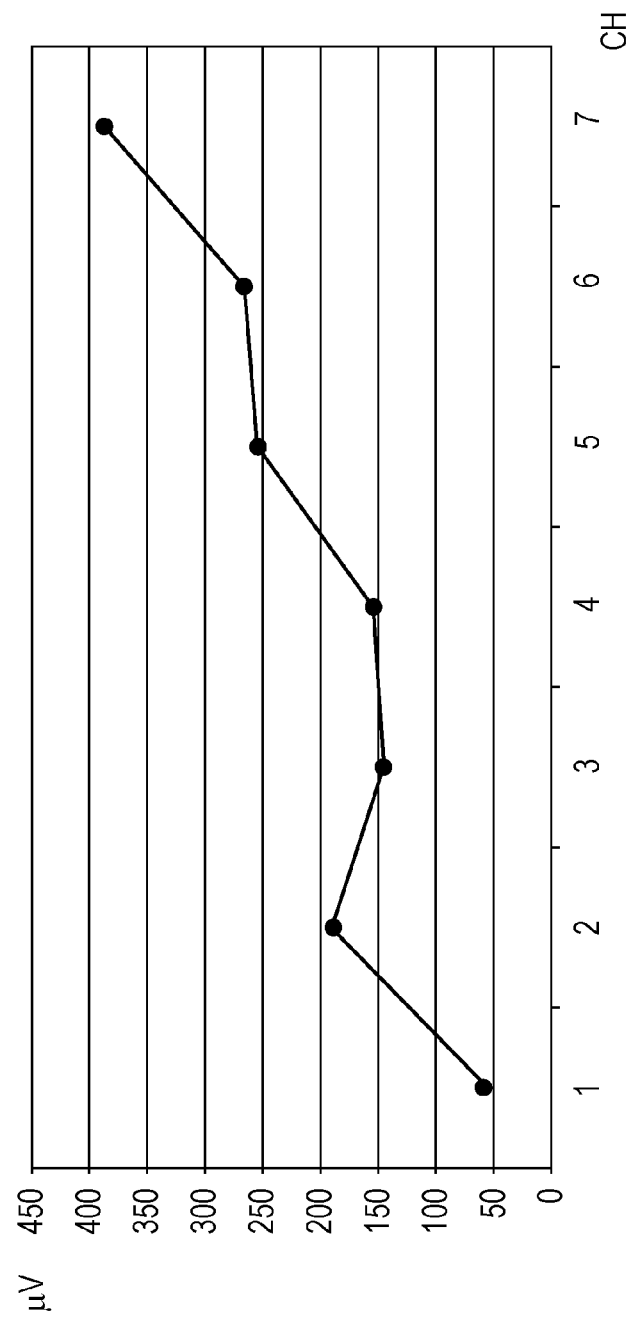
FIG. 6 illustrates an example of a myopotential measured by a biopotential measuring unit of the embodiment.

The biopotential measuring unit 401 measures a myopotential set at multiple locations of the wrist of the user 10 using the multiple electrodes 310. FIG. 6 illustrates an example of the myopotential set measured by the biopotential measuring unit 401. In the graph of FIG. 6, the ordinate represents the magnitude of potential in μV and the abscissa represents a channel number of the measurement electrode 311. The channel numbers correspond to numbers respectively assigned to the seven measurement electrodes 311 as illustrated in FIG. 3C and FIG. 3D.

The measured potential transmitter 402 transmits the measured myopotential set to the action determination device 101.

Step S102

The measured potential receiver 403 receives the myopotential set transmitted from the measured potential transmitter 402 and then transfers the received myopotential set to the action detector 404.

The action detector 404 detects a myopotential equal to or above a predetermined threshold potential from the received myopotential set. The predetermined threshold potential is higher than a myopotential when the user 10 is in a normal condition, and still falls within a potential range within which the user 10 takes an intentional action. The predetermined threshold potential is set based on potentials pre-measured at the user 10 who wears the input device 100 or at a location where the user 10 wears the input device 100.

For example, the action detector 404 determines whether a myopotential equal to or above the predetermined threshold potential is included in the myopotential set. If a myopotential equal to or above the predetermined threshold potential is included in the myopotential set, the action detector 404 acquires time at which the myopotential set is measured. The time acquired herein may have a certain width of time. From among multiple myopotential sets successively measured by the biopotential measuring unit 401, the action detector 404 determines the myopotential set measured at the acquired time to be a myopotential set when the user 10 takes any kind of action (gesture).

If the predetermined threshold potential in the example of FIG. 6 is "200", potentials at channels 5 through 7 are above the threshold potential. The action detector 404 thus determines the myopotential set including the channels 1 through 7 having potentials higher than the threshold potential to be the myopotential set when the user 10 takes any kind of action (gesture).

Step S103

Figure 7:
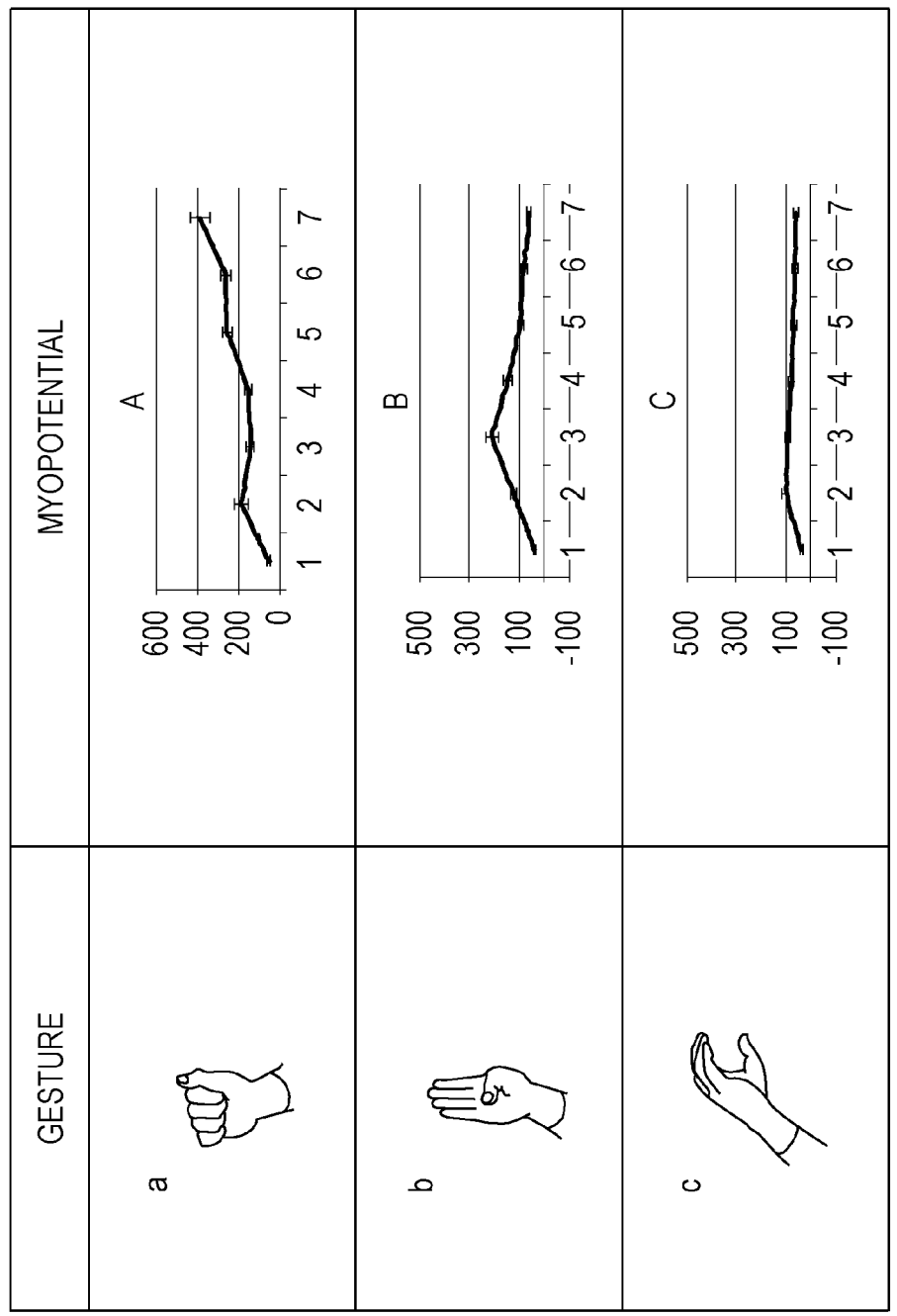
FIG. 7 illustrates an example of a determination criterion of the embodiment.

The action determination unit 405 determines a gesture corresponding to the myopotential set detected by the action detector 404 by referencing the determination criteria stored at the criteria storage unit 406. FIG. 7 illustrates an example of the determination criteria stored on the criteria storage unit 406 of the embodiment. FIG. 7 lists as the determination criteria the magnitudes of the channels (the myopotential pattern) corresponding to gestures including a gesture of making a first (stone), and a gesture of bending the thumb with the other four fingers stretched open.

The action determination unit 405 references the determination criteria stored on the criteria storage unit 406 illustrated in FIG. 7, and determines a gesture corresponding to the myopotential set detected by the action detector 404 and illustrated in FIG. 6 using a pattern matching technique, for example. The action determination unit 405 references the determination criteria of FIG. 7, thereby determining the gesture corresponding to the myopotential set of FIG. 6 (a gesture of making a fist).

The determination result transmitter 407 transmits the gesture determined by the action determination unit 405 to the control target device 102.

Step S104

The determination result receiver 408 receives from the determination result transmitter 407 the gesture determined by the action determination unit 405.

The device controller 409 determines an operation corresponding to the gesture of the user 10 by referencing the pre-stored operation criteria. The device controller 409 executes the operation by controlling the device function execution unit 410.

FIG. 8 illustrates an example of the operation criteria in the embodiment. In the example of FIG. 8, the gestures are associated with the operations of the control target device 102. For example, the operations include a power-on operation, a power-off operation, an adjustment of volume level (turning up or down the volume), and screen operations (advancing the pages, a zoom-in operation, and a zoom-out operation).

Advantageous Effects

As described above in the input device 100 of the embodiment, the position determination unit 303 having a shape to be engaged with at least part of the periphery of the styloid process of ulna 11 of the user 10 is located close to the first opening 304. The user 10 may wear the input device 100 such that the position determination unit 303 is engaged with the styloid process of ulna 11. In other words, the position determination unit 303 assists the user 10 to wear the input device 100 at the appropriate location. A displacement of the input device 100 in the mounting location thereof (such as a rotation of the input device 100 around the wrist) is controlled with the position determination unit 303 engaged with the styloid process of ulna 11. As a result, the input device 100 stabilizes the contact positions of the electrodes 310 with the position determination unit 303 when the input device 100 is worn around the wrist of the user 10.

If the input device 100 slides around the wrist in the mounting operation of the input device 100, the measurement electrode 311 is displaced in position. Even if the user 10 makes the same gesture, the measured potential varies greatly. As a result, the recognition accuracy of gesture is degraded. The input device 100 of the embodiment is mounted with the position determination unit 303 engaged with the styloid process of ulna 11. This arrangement makes it difficult for the input device 100 to slide around the wrist, and controls a decrease in the recognition accuracy of gesture responsive to a change in the location of the measurement electrode 311.

In the input device 100 of the embodiment, the reference electrode 312 and the ground electrode 313 are aligned with the position determination unit 303 in the axial direction of the band 302. When the input device 100 is worn around the wrist of the user 10 such that the position determination unit 303 is engaged with the styloid process of ulna 11, the reference electrode 312 and the ground electrode 313 is placed on the ulna. When an action potential is measured from the surface of the living body, an electrode serving as a reference is desirably placed on an immobile skin portion, such as the skin on a bone, other than a target muscle. (Reference is made to Reference is also made to Tetsuji FUJIWARA, "*Electromyogram and Evoked Potential Manual*" Kinpodo, July 2004, p. 40). With the reference electrode 312 placed on the ulna of the user 10, the input device 100 appropriately normalizes the biopotential measured using the measurement electrode 311. With the ground electrode 313 placed on the ulna of the user 10, the input device 100 appropriately grounds electronic devices.

In the input device 100 of the embodiment, the measurement electrode 311 is located at a center position between the first opening 304 and the second opening 305 along the axial direction or at a position closer to the second opening 305 than to the center position. When the input device 100 is worn around the wrist such that the position determination unit 303 is engaged with the styloid process of ulna 11, the measurement electrode 311 is spaced apart from the hand joint of the user 10. This arrangement controls a displacement in the contact position of the measurement electrode 311 or keeps the measurement electrode 311 from lifting off the skin of the user 10 when the user 10 bends or stretches the hand joint. More specifically, the input device 100 is stabilized in the contact position of the measurement electrode 311, thereby reliably measuring the biopotential.

In the input device 100 of the embodiment, the position determination unit 303 is a cutout formed along the edge of the band 302 along the first opening 304. The input device 100 is worn with the cutout engaged with the styloid process of ulna 11, and the contact positions of the multiple electrodes 310 are thus stabilized.

First Modification

A first modification of the embodiment is described below. The first modification is different from the embodiment in that the band of an input device 100A of the first modification has a marking for the user to wear the input device 100 at an appropriate location. The following discussion of the input device 100A of the first modification focuses on a difference from the input device 100 of the embodiment.

Figure 9:
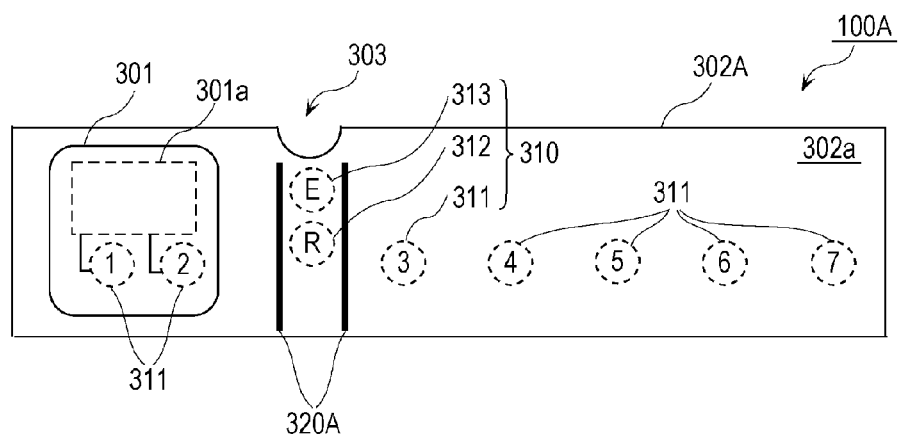
FIG. 9 illustrates an input device of a first modification of the embodiment with a band thereof unfolded.

FIG. 9 illustrates the input device 100A of the first modification of the embodiment with a band 302A thereof unfolded. In FIG. 9, wirings electrically connecting elements are not illustrated. Elements similar to or identical to those illustrated in FIG. 3C and FIG. 3D are designated with the same reference numerals and the discussion thereof is omitted as appropriate.

A marking 320A is attached to the external surface 302a of the band 302A of the input device 100A. The marking 320A indicates the locations of the reference electrode 312 and the ground electrode 313 in alignment with the position determination unit 303.

In the first modification, the marking 320A is shaped to extend along the ulna of the user 10. With the marking 320A placed along the ulna, the input device 100A is mounted at an appropriate location.

In the input device 100A of the first modification, the marking 320A indicating the locations of the reference electrode 312 and the ground electrode 313 is attached to the external surface 302a of the band 302A. The user 10 may thus easily wear the input device 100A such that the reference electrode 312 and the ground electrode 313 are placed along the ulna.

Second Modification

A second modification of the embodiment is described below. The second modification is different from the embodiment in that an input device 100B of the second modification includes position determination units respectively for the right and left wrists of the user 10. The following discussion of the input device 100B of the second modification focuses on a difference from the input device 100 of the embodiment.

Figure 10:
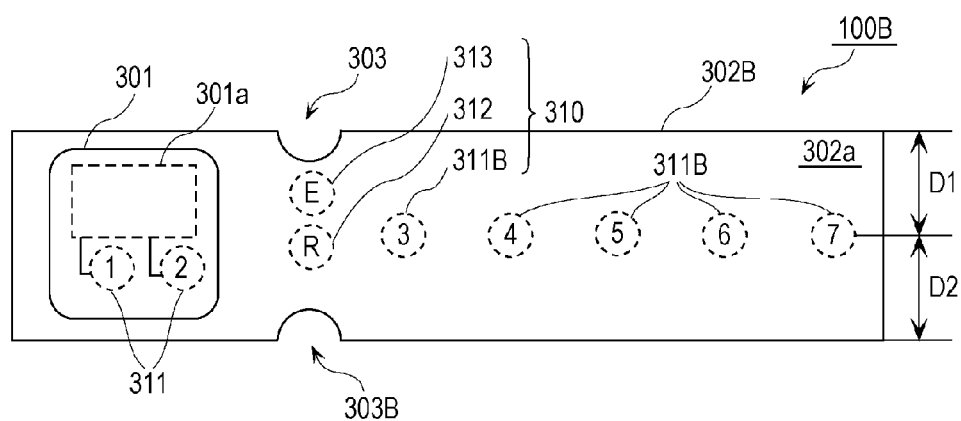
FIG. 10 illustrates an input device of a second modification of the embodiment with a band thereof unfolded.

FIG. 10 illustrates the input device 100B of the second modification of the embodiment with the band 302 thereof unfolded. In FIG. 10, wirings electrically connecting elements are not illustrated. In FIG. 10, elements similar to or identical to those illustrated in FIG. 3C and FIG. 3D are designated with the same reference numerals and the discussion thereof is omitted as appropriate.

Referring to FIG. 10, the input device 100B of the second modification includes a position determination unit 303B in addition to the position determination unit 303. The position determination unit 303 corresponds to a first position determination unit and the position determination unit 303B corresponds to a second position determination unit. As the position determination unit 303, the position determination unit 303B is shaped to engage with part of the periphery of the styloid process of ulna 11 of the user 10. In the second modification, the position determination unit 303 is configured to engage with the styloid process of ulna of the right wrist of the user 10, and the position determination unit 303B is configured to engage with the styloid process of ulna of the left wrist of the user 10.

The position determination unit 303B is located closer to the second opening 305. More specifically, the position determination unit 303B is a cutout formed along the edge of the band 302B at the second opening 305. In other words, the position determination unit 303B is the cutout formed at the second side extending along the longitudinal direction of the band 302B. The position determination unit 303 and the position determination unit 303B are respectively formed on the sides of the band 302B opposed to each other.

Referring to FIG. 10, the measurement electrodes 311B are located along a line equidistant from the two sides (the first side and second side) along the longitudinal direction of the band 302. In other words, the measurement electrodes 311B are located at a center point between the first opening 304 and the second opening 305 in the axial direction of the tubular shape. More specifically, a distance D1 between the measurement electrodes 311B and the first side is equal to a distance D2 between the measurement electrodes 311B and the second side. The center point does not necessarily have to be strictly central, but may be approximately central. Similarly, the word equidistant does not necessarily have to be strictly equidistant, but may be approximately equidistant.

The input device 100B of the second modification includes the two position determination units (the position determination unit 303 and the position determination unit 303B) corresponding to the right wrist and left wrist of the user 10. Regardless of whether the input device 100B is worn around the right wrist or left wrist, the contact positions of the electrodes are stabilized.

Third Modification

A third modification of the embodiment is described below. The third modification is different from the embodiment in that a band of an input device 100C of the third modification includes a first band portion and a second band portion different from each other in flexibility. The following discussion of the input device 100C of the third modification focuses on a difference from the input device 100 of the embodiment.

Figure 11:
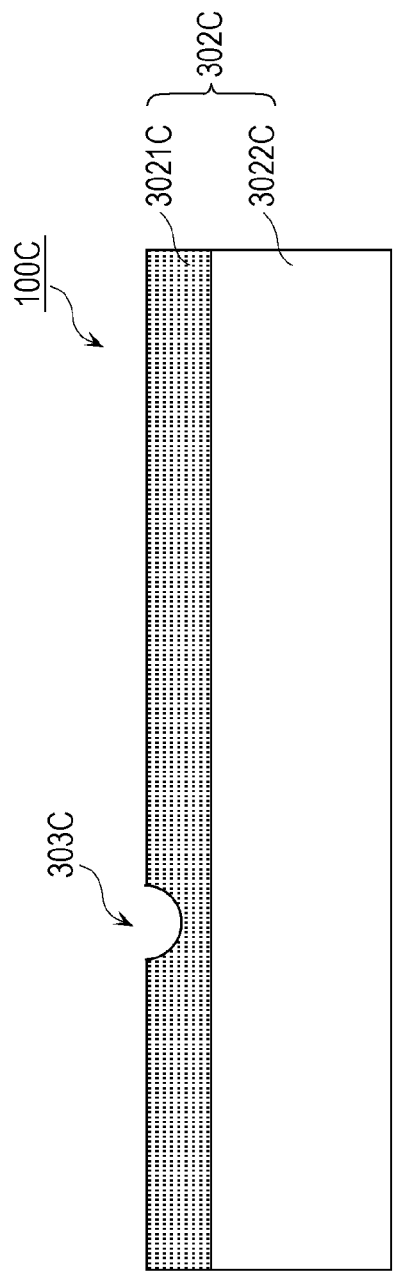
FIG. 11 illustrates an input device of a third modification of the embodiment with a band thereof unfolded.

FIG. 11 illustrates the input device 100C of the third modification of the embodiment with a band 302C thereof unfolded. In FIG. 11, elements other than the band 302C and the position determination unit 303C are not illustrated.

The band 302C includes a first band portion 3021C and a second band portion 3022C lower in flexibility than the first band portion 3021C. The first band portion 3021C and the second band portion 3022C are together worn around the wrist of the user 10.

The position determination unit 303C is formed in the first band portion 3021C. In the third modification, the position determination unit 303C is a cutout formed along the side extending along the longitudinal direction of the first band portion 3021C.

In the input device 100C of the third modification, the position determination unit 303C is formed in the first band portion 3021C that is higher in flexibility than the second band portion 3022C. The position determination unit 303C is configured to flexibly engage with a difference in the shape of the styloid process of ulna 11, and thus fits with the styloid process of ulna 11.

Fourth Modification

A fourth modification of the embodiment is described below. The position determination unit in the fourth modification is different from the position determination unit in the embodiment. The following discussion of the input device 100D of the fourth modification focuses on a difference from the input device 100 of the embodiment.

Figure 12:
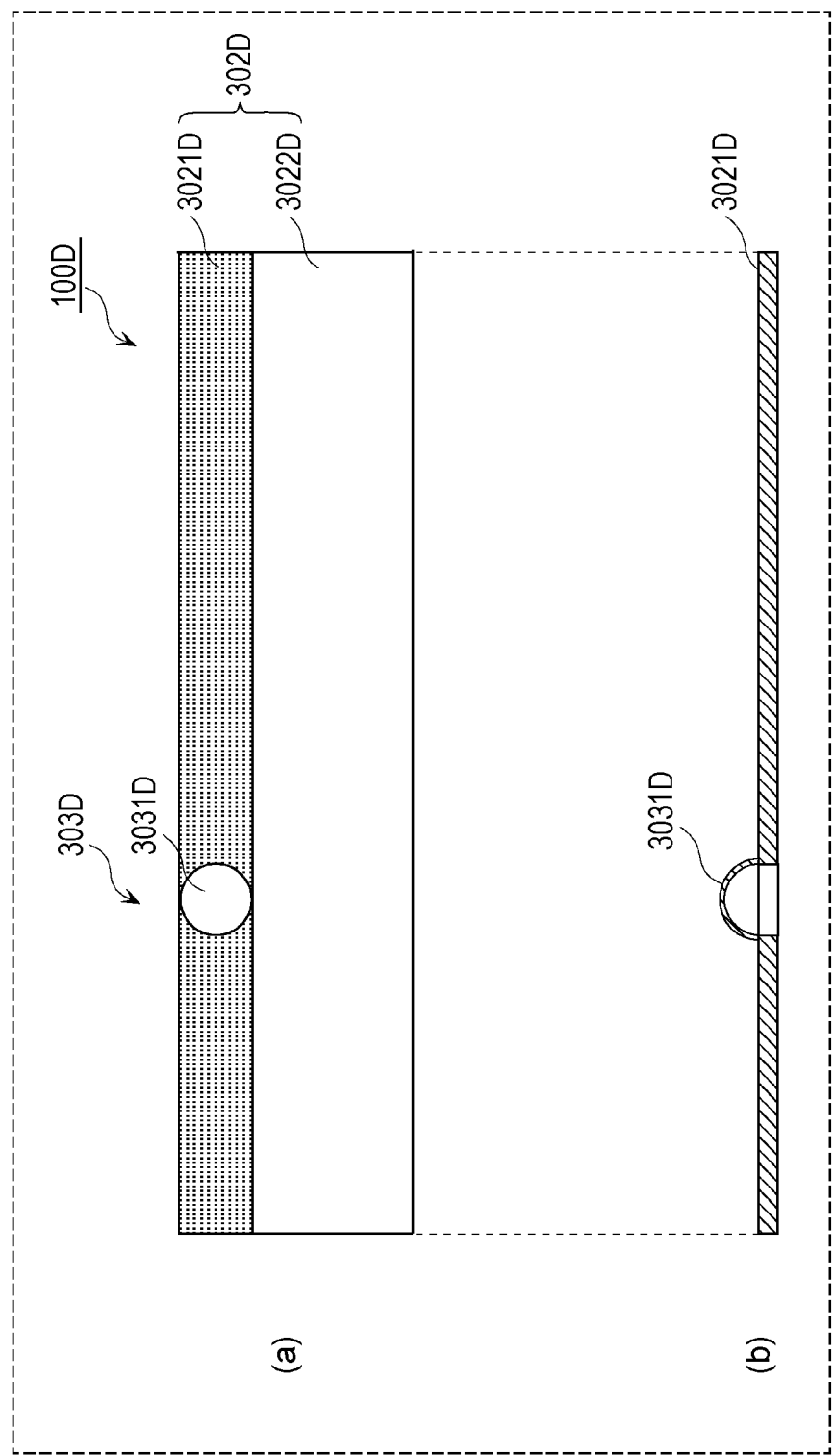
FIG. 12 illustrates an input device of a fourth modification of the embodiment with a band thereof unfolded.

FIG. 12 illustrates the input device 100D of the fourth modification of the embodiment with a band 302D thereof unfolded. More specifically, a portion (a) of FIG. 12 illustrates the input device 100D viewed from inside. A portion (b) of FIG. 12 is a sectional view of the input device 100D taken along the longitudinal direction. As illustrated in FIG. 12, elements other than the band 302D and the position determination unit 303D are not illustrated.

The band 302D includes a first band portion 3021D and a second band portion 3022D that is lower in flexibility than the first band portion 3021D. The first band portion 3021D and the second band portion 3022D are wound together around the wrist of the user 10.

The position determination unit 303D is a circular recess formed in the internal surface of the first band portion 3021D that is configured to be in contact with the wrist of the user 10. In the fourth modification, the recess is a through-hole penetrating through the first band portion 3021D. The input device 100D is worn around the wrist of the user 10 such that the styloid process of ulna 11 is received in the position determination unit 303D.

The position determination unit 303D includes a cap 3031D that closes the through-hole on the external surface of the first band portion 3021D. At least part of the cap 3031D is transparent. The cap 3031D may detachably close the through-hole.

In the input device 100D of the fourth modification, the position determination unit 303D is the recess formed in the internal surface of the first band portion 3021D (the through-hole in the fourth modification). The input device 100 is thus worn around the wrist of the user 10 such that the recess (through-hole) receives the styloid process of ulna 11. The contact positions of the electrodes are thus stabilized.

In the input device 100D of the fourth modification, at least part of the cap 3031D is transparent. When the user 10 mounts the input device 100D on the wrist, he or she may cause the through-hole to receive the styloid process of ulna 11 while watching the styloid process of ulna 11. More specifically, the cap 3031D assists the user 10 to mount the input device 100D at an appropriate location.

The cap 3031D detachably closes the through-hole. When the user 10 wears the input device 100D around his or her wrist, the user 10 may cause the through-hole to receive the styloid process of ulna by opening the cap 3031D. The cap 3031D thus assists the user 10 to wear the input device 100D at an appropriate position.

If the band is not flexible enough, the styloid process of ulna 11 may cause a gap between the band and the wrist when the input device 100D is worn around the wrist of the user 10. Since the multiple electrodes 310 fail to be in contact with the skin of the user 10 in such a case, there is a possibility that the biopotential is not precisely measured. In the fourth modification, the recess (through-hole) is formed in the first band portion 3021D. This arrangement ensures that the multiple electrodes 310 remains in contact with the user 10.

Fifth Modification

A fifth modification of the embodiment is described below. The reference electrode is desirably placed at a location where any potential is difficult to be generated when the finger or hand moves. An input device 100E of the fifth modification includes and selectively uses multiple reference electrodes to stably measure the biopotential. The following discussion of the input device 100E of the fifth modification focuses on a difference from the input device 100 of the embodiment.

Figure 13:
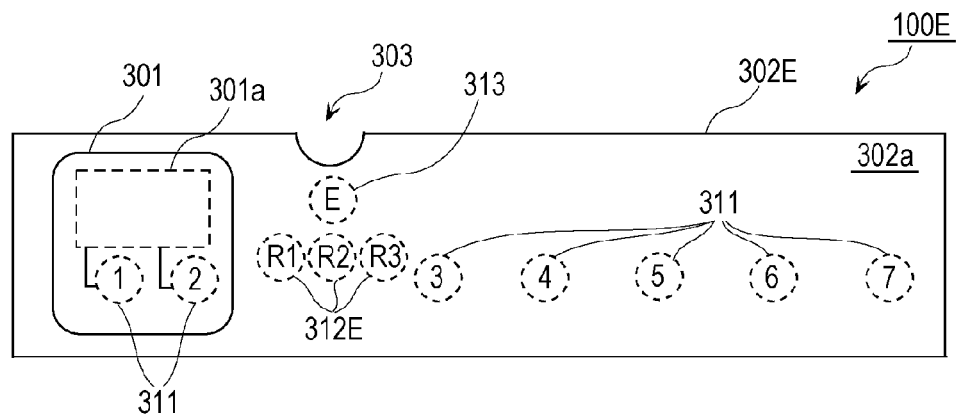
FIG. 13 illustrates an input device of a fifth modification of the embodiment with a band thereof unfolded.

FIG. 13 illustrates the input device 100E of the fifth modification of the embodiment with a band 302E thereof unfolded. Referring to FIG. 13, wirings electrically connecting elements are not illustrated. As illustrated in FIG. 13, elements identical to those of FIG. 3C and FIG. 3D are designated with the same reference numerals and the discussion thereof is omitted as appropriate.

Referring to FIG. 13, the band 302E includes multiple reference electrodes 312E near the position determination unit 303. Each of the reference electrodes 312E measures the reference potential that is used to normalize the biopotential measured using each of the measurement electrodes 311.

Figure 14:
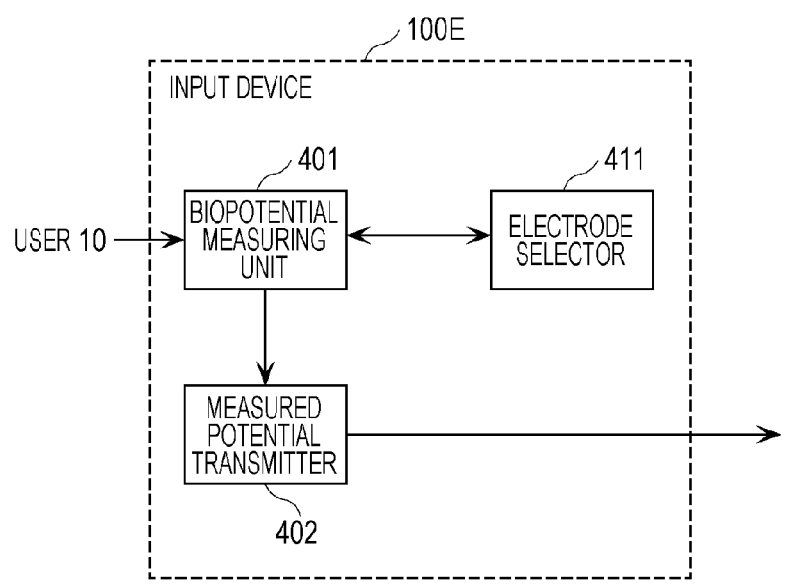
FIG. 14 is a functional block diagram illustrating the input device of the fifth modification of the embodiment.

FIG. 14 is a functional block diagram illustrating the input device 100E of the fifth modification of the embodiment. In FIG. 14, elements similar to or identical to those in FIG. 4 are designated with the same reference numerals and the discussion thereof is omitted as appropriate.

The input device 100E includes a biopotential measuring unit 401, a measured potential transmitter 402, and an electrode selector 411.

The electrode selector 411 selects one from the reference electrodes 312E. For example, the electrode selector 411 selects a reference electrode that measures the lowest potential from among the potentials measured when a finger is moved.

The selection of the reference electrode may be performed when the user 10 explicitly instructs calibration to be performed. The input device 100E then measures myopotentials using the reference electrodes 312E for a duration of several seconds, for example. The electrode selector 411 then selects the reference electrode that measures the lowest myopotential.

The input device 100E may automatically perform the selection of the reference electrode. In such a case, the reference electrode that measures the lowest myopotential when the action detector 404 detects an action is automatically selected.

The biopotential measuring unit 401 normalizes the biopotential measured by the measurement electrode 311 using the reference potential measured using the selected reference electrode. More specifically, the biopotential measuring unit 401 selectively uses one of the reference potentials measured using the reference electrodes 312E to normalize the biopotential measured using the measurement electrode 311. More specifically, the biopotential measuring unit 401 subtracts the potential of the selected reference electrode from the potential of each of the measurement electrodes 311, thereby calculating the normalized biopotential.

As described above, the input device 100E of the fifth modification selectively uses one of the reference potentials measured by the reference electrodes 312E to normalize the biopotential measured using the measurement electrode 311. The biopotential is thus normalized using an appropriate reference potential.

Sixth Modification

A sixth modification of the embodiment is described below. The sixth modification is different from the embodiment and the fifth modification in that an input device 100F of the sixth modification is includes multiple ground electrodes in addition to multiple reference electrodes. The following discussion of the input device 100F of the sixth modification focuses on a difference from the embodiment and the fifth modification.

Figure 15:
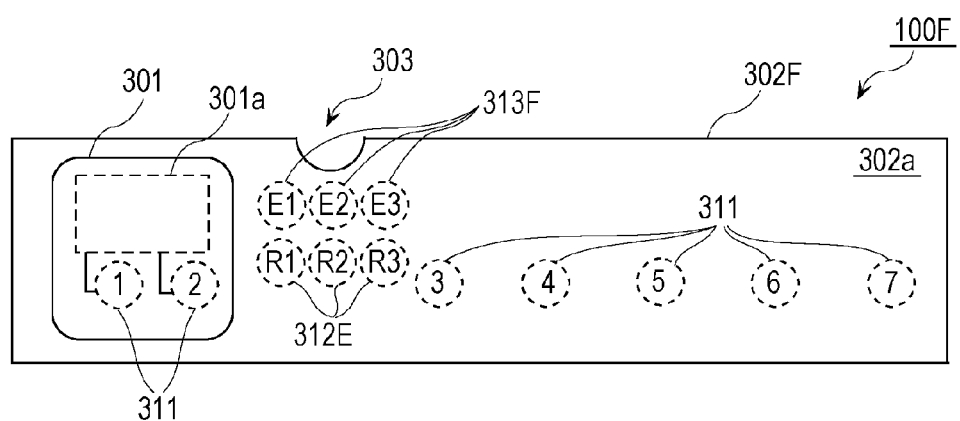
FIG. 15 illustrates an input device of a sixth modification of the embodiment with a band thereof unfolded.

FIG. 15 illustrates the input device 100F of the fifth modification of the embodiment with a band 302F thereof unfolded. Referring to FIG. 15, wirings electrically connecting elements are not illustrated. As illustrated in FIG. 15, elements identical to those of FIG. 3C, FIG. 3D and FIG. 13 are designated with the same reference numerals and the discussion thereof is omitted as appropriate.

Referring to FIG. 15, the band 302F includes multiple reference electrodes 312E and multiple ground electrodes 313F near the position determination unit 303.

The input device 100F thus includes the multiple ground electrodes 313F. Electronic devices included in the input device 100F are reliably grounded.

One of the ground electrodes 313F may be selectively used four grounding. In such a case, a ground electrode having a lowest variation in potential caused by the motion of the hand may be used.

Seventh Modification

A seventh modification of the embodiment is described below. The seventh modification is different from the embodiment in the shape of the position determination unit. The following discussion of an input device 1000 of the seventh modification focuses on a difference from the input device 100 of the embodiment.

Figure 16A:
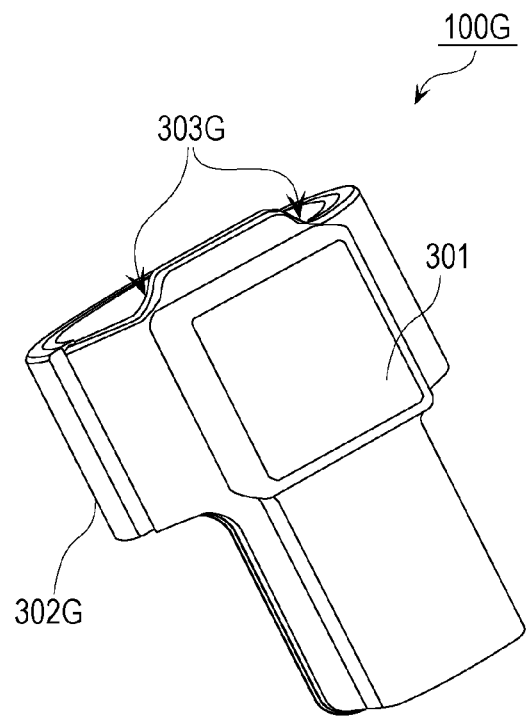
FIG. 16A and FIG. 16B are perspective views of an input device of a seventh modification of the embodiment.
Figure 16B:
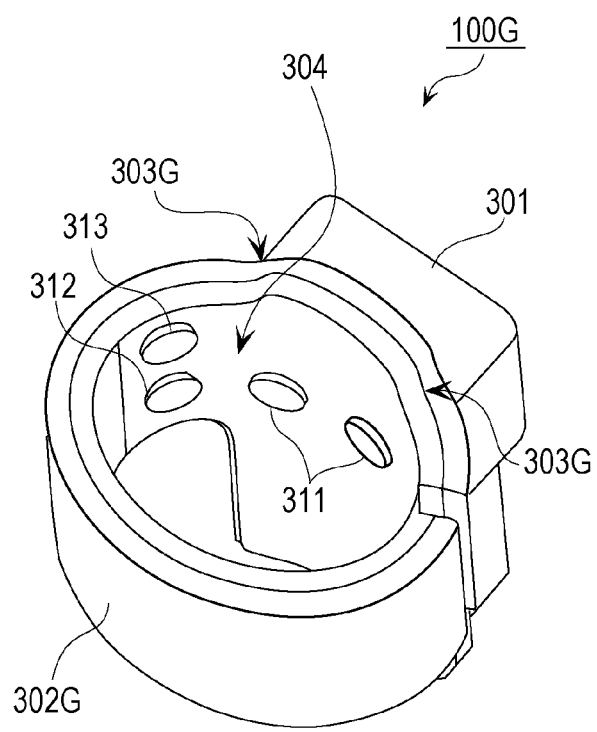

FIG. 16A and FIG. 16B are perspective views of the input device 100G of the seventh modification of the embodiment. More specifically, FIG. 16A and FIG. 16B are the perspective views of the input device 100G viewed from different directions. As illustrated in FIG. 16A and FIG. 16B, elements similar to or identical to those of FIG. 3A and FIG. 3B are designated with the same reference numerals and the discussion thereof is omitted as appropriate.

The input device 100G includes a device body 301, a band 302G, two position determination units 303G, multiple measurement electrodes 311, a reference electrode 312, and a ground electrode 313.

The position determination units 303G are formed at the end of the band 302G defining the first opening 304. The position determination units 303G are herein formed along a side longitudinally extending along the band 302G. More specifically, the position determination units 303G are formed of a side wall extending from the longitudinal side of the band 302G across the width thereof to the other longitudinal side. Each of the position determination units 303G has an arc edge that partially engages with the end of the styloid process of ulna 11 of the user 10.

The input device 100G of the seventh modification thus includes the position determination units 303G having the arc edge. The position determination units 303G having the arc edge engage with the styloid process of ulna 11 when the input device 1000 is worn around the wrist of the user 10. The contact position of the input device 1000 is thus stabilized.

Eighth Modification

An eighth modification of the embodiment is described below. An input device 100H of the eight modification is different from the embodiment and the second modification in that the input device 100H includes a display that displays information to the user. The following discussion of an input device 100H of the eighth modification focuses on a difference from the embodiment and the second modification.

In the eighth modification described herein, the display displays time information. The information displayed on the display is not limited to the time information.

Figure 17:
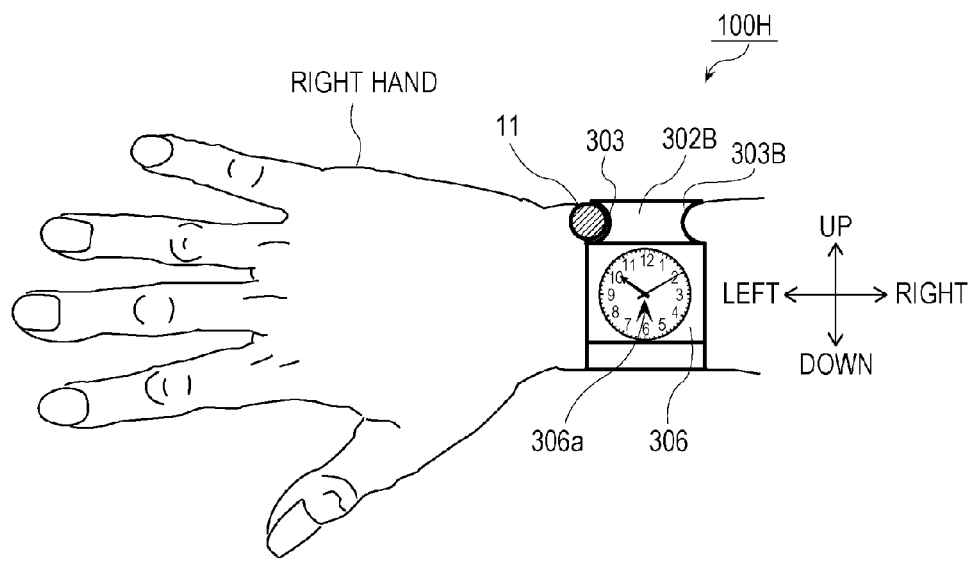
FIG. 17 illustrates an input device of an eighth modification of the embodiment worn around the right wrist of a user.
Figure 18:
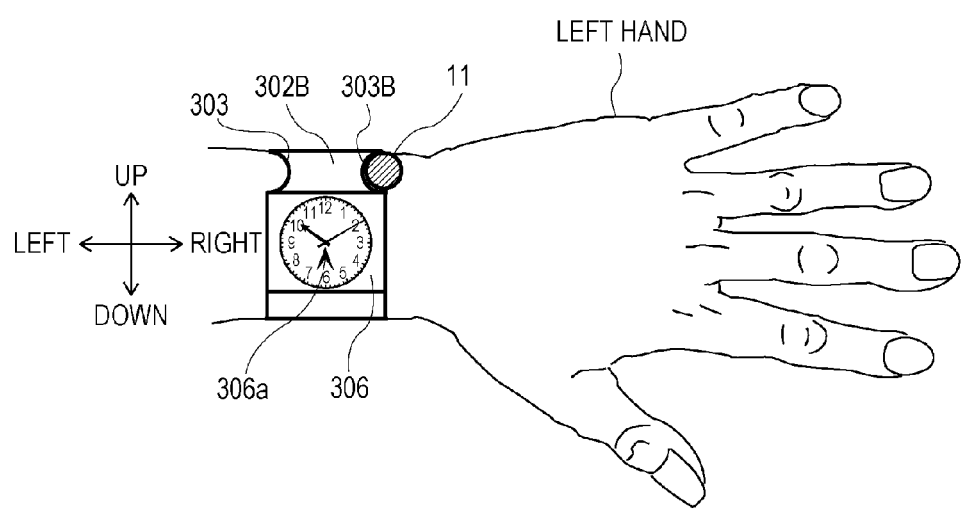
FIG. 18 illustrates an input device of the eighth modification of the embodiment worn around the left wrist of a user.

FIG. 17 illustrates the input device 100H of the eighth modification of the embodiment worn around the right wrist of the user 10. FIG. 18 illustrates the input device 100H of the eighth modification of the embodiment worn around the left wrist of the user 10. As illustrated in FIG. 17 and FIG. 18, elements similar to or identical to those of FIG. 3A, FIG. 3B, FIG. 3C, FIG. 3D, and FIG. 10 are designated with the same reference numerals and the discussion thereof is omitted as appropriate.

The input device 100H includes the band 302B, the position determination units 303 and 303B, and multiple electrodes 310. The input device 100H further includes a display 306 on an external surface of a tubular structure formed of the band 3026.

The display 306 display an image (time screen indicating time information here). As illustrated in FIG. 17 and FIG. 18, the display 306 has an area extending in a right-left direction (in a horizontal direction) and in an up-down side direction (in a vertical direction).

The position determination units 303 and 303B are located above the center 306a of the display 306. The center 306a indicates a substantially central position of the display 306 in a plan view of the display 306. More specifically, the position determination unit 303 of the right wrist is located at the top left of the display 306. The position determination unit 303B of the left wrist is located at the top right of the display 306.

The display 306 displays a screen in alignment in which the position determination units 303 and 303B are located above the center of the screen. In other words, the screen (time display screen) displayed by the display 306 is aligned such that the position determination units 303 and 303B are located above the screen.

The user 10 wears the input device 100H of the eighth modification such that the position determination unit 303 engages with the styloid process of ulna 11. In this way, the input device 100 is worn such that the styloid process of ulna 11 comes above the center of the display 306. In this way, the user is assisted to wear the input device 100H such that the display 306 is located in a correct alignment.

The input device 100H of the eighth modification is worn around the wrist of the user 10 such that the position determination unit 303 is engaged with the styloid process of ulna 11. In this position of the input device 100H, the screen is displayed such that the styloid process of ulna 11 comes above the center of the display 306. In other words, the user 10 may easily recognize the screen.

Other Modifications

The input devices and control system of the embodiment and the modifications thereof are described above. The disclosure is not limited to the embodiments and modifications. A variety of changes and modifications to the embodiment and modifications may be apparent to those skilled in the art without departing from the scope of the disclosure. A combination of elements in the embodiment and modifications may form an embodiment. Such an embodiment may also fall within the scope of the disclosure.

In the embodiment and modifications, the input device includes multiple electrodes. The disclosure is not limited to this arrangement. The input device may include a single electrode only. In such a case, the biopotential is measured using that electrode.

In the embodiment and modifications, the operation of the control target device 102 is determined based on the determination criteria (see FIG. 7) to determine a gesture from the biopotential and the operation criteria (see FIG. 8) to determine an operation responsive to the gesture. The disclosure is not limited to this method. For example, the action determination device 101 may skip the gesture determination and directly determine the operation from the biopotential.

Figure 19:
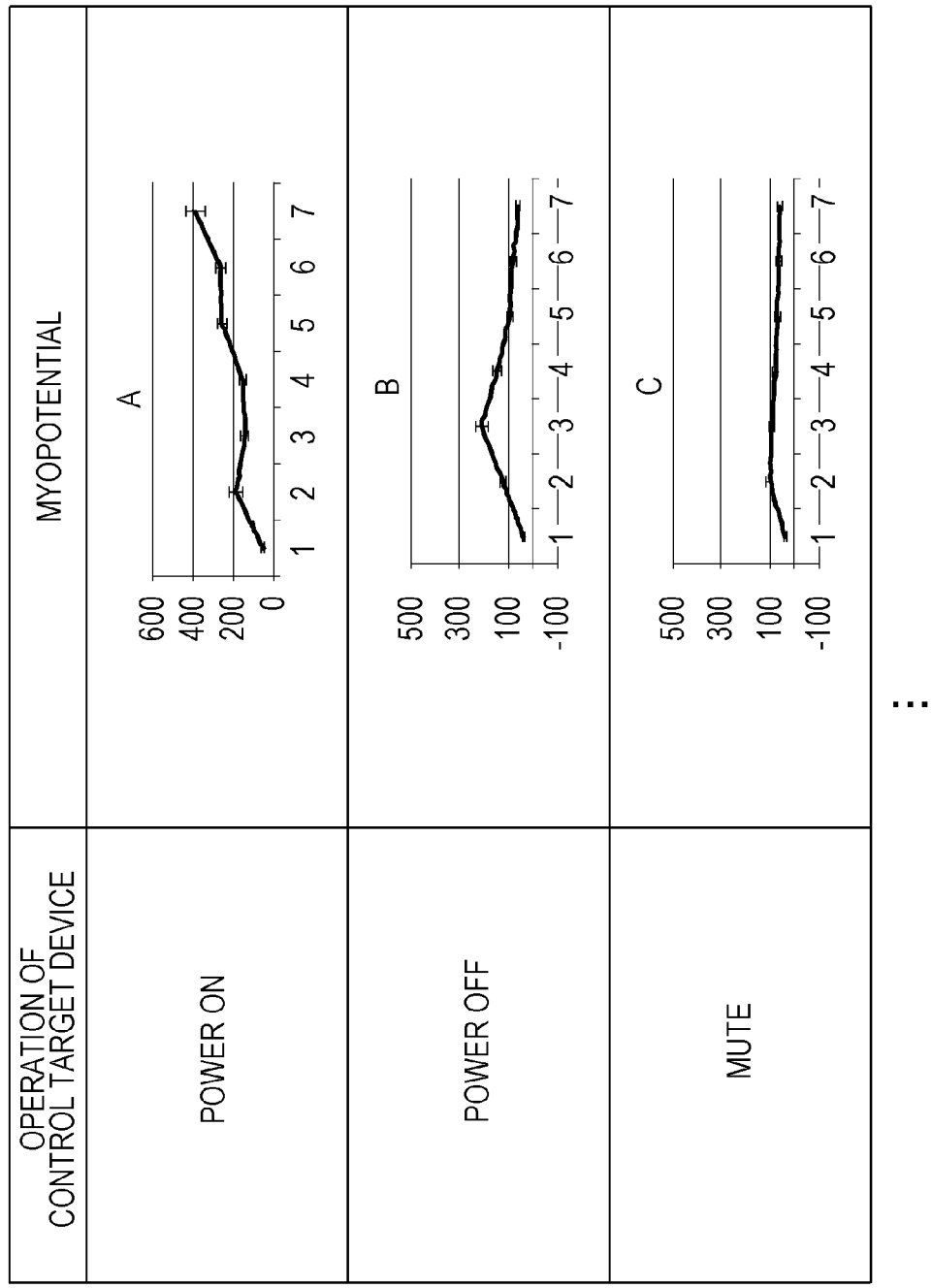
FIG. 19 illustrates an example of an determination criterion in another modification of the embodiment.

The criteria storage unit 406 may store information of FIG. 19. FIG. 19 illustrates an example of the determination criteria in another modification of the embodiment. The determination criteria herein are information that associates a myopotential pattern of the user with the operation of the control target device. The action determination unit 405 references the determination criteria of FIG. 19, and determines the operation of the control target device 102 from a myopotential set of the user.

In the embodiment and modifications, the device body and the band are integrally formed as a unitary body. The disclosure is not limited to this arrangement. The device body and the band may be set to be separate. In such a case, the device body and the band are electrically and physically connected.

Figure 20:
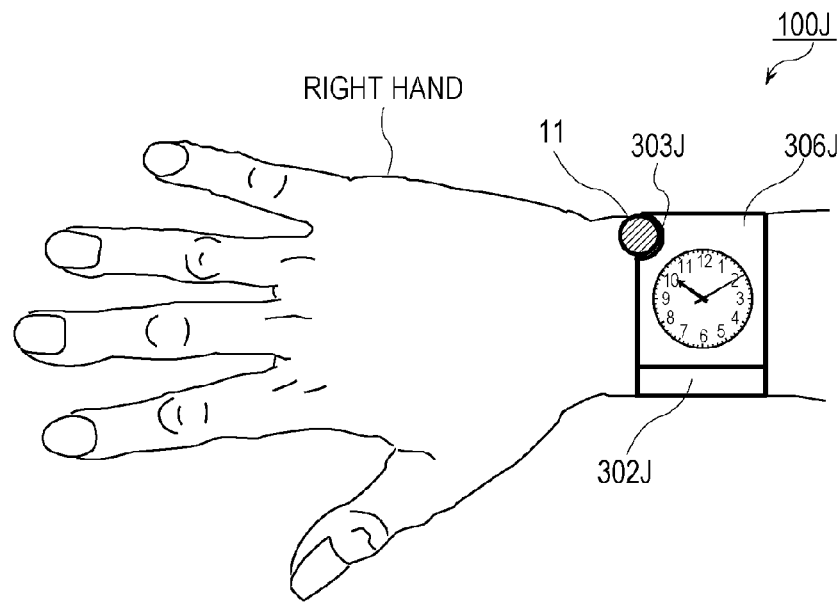
FIG. 20 illustrates an example of a position determination unit in another modification of the embodiment.

In the embodiment and modifications, the position determination unit is formed in the band. Alternatively, the position determination unit may be formed in the device body or the display. In an input device 100J of FIG. 20, a position determination unit 303J is formed in a display 306J. In such a case, no position determination unit is formed in a band 302J. In this way, the display 306J extends beyond the styloid process of ulna 11, and the display 306J is more easily visible to the user.

In the eighth modification, the display is formed on part of the external surface of the tubular structure worn around the wrist of the user. Alternatively, the display may be formed on the entire external surface. For example, the external surface of the band may be a display.

In the eighth modification, the display is a liquid-crystal display. The disclosure is not limited to this arrangement. The display may be a mechanical analog watch.

In the embodiment and modifications, the control system includes the input device, the action determination device, and the control target device. The control system is not limited to this arrangement. For example, the input device may include the action determination device. The input device may include the action determination device and the control target device. If the input device is a smart watch, the user may operate the smart watch by a gesture of the forearm.

In the embodiment, the input device includes the position determination unit such that the input device is worn around the right wrist of the user. The position determination unit may be disposed such that the input device is worn on the left wrist of the user. In other words, the input device may be of a right-wrist-worn type or a left-wrist-worn type. As described with reference to the second and seventh modifications, the input device may be of a both-wrist-worn type.

Figure 21:
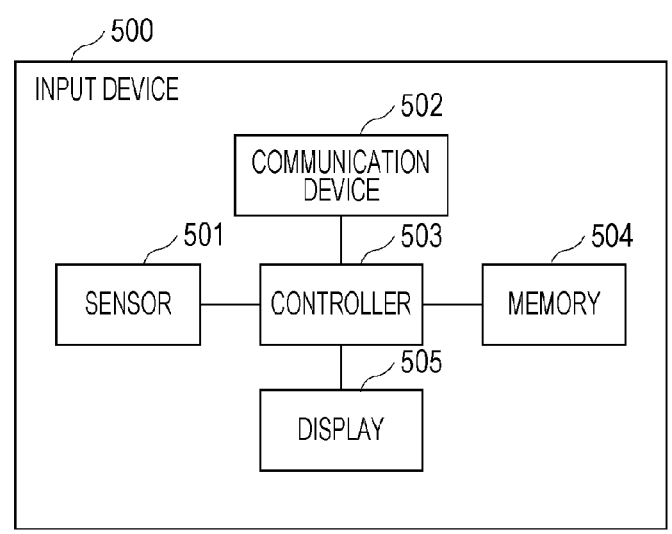
FIG. 21 illustrates an example of a software configuration of the input device.

The input device may have a hardware configuration of FIG. 21. As illustrated in FIG. 21, an input device 500 includes a sensor 501, a communication device 502, a controller 503, a memory 504, and a display 505.

The sensor 501 measures the biopotential of the user. The sensor 501 works as the biopotential measuring unit 401 described with reference to the embodiment.

The communication device 502 transmits the measured biopotential. The communication device 502 works as the measured potential transmitter 402 described with reference to the embodiment. The communication device 502 may be a wireless communication adaptor.

The controller 503 controls the sensor 501, the communication device 502, the memory 504, and the display 505. The controller 503 may be a dedicated circuit or a general-purpose processor.

The memory 504 stores a program used by the controller 503 and data.

The display 505 displays an image. The display 505 works as the display 306 described with reference to the eighth modification. The display 505 may be a liquid-crystal display or an organic electroluminescence (EL) display. The display 505 may also be a touch display.

The input device of the embodiment of the disclosure finds wide applications as a wrist-worn type device for gesture inputting. More specifically, the input device may be applied to operate home electronics, such as a television receiver, and a mobile terminal, such as a smart phone.

What is claimed is:

1. A wrist-worn input device measuring a biopotential for use in inputting a gesture, comprising:
    a band that forms at least part of a tubular structure having a first opening and a second opening at two ends thereof in an axial direction thereof;
    one or more electrodes open to an internal surface of the band;
    a first position determiner that is located close to the first opening and has a shape to be engaged with at least part of a periphery of the styloid process of ulna of a user;
    a measurer that measures the biopotential of the user using the one or more electrodes; and
    an outputter that outputs the biopotential of the user measured by the measurer,
    wherein the one or more electrodes include at least one measurement electrode, and
    wherein the at least one measurement electrode is located at a center point between the first opening and the second opening along the axial direction or located at a point closer to the second opening than to the center point along the axial direction.

2. The wrist-worn input device according to claim 1, wherein the one or more electrodes comprise at least one reference electrode,
    wherein the at least one reference electrode is located in alignment with the first position determiner along the axial direction and measures a reference potential that is used to normalize the biopotential measured using the at least one measurement electrode, and
    wherein the first position determiner and the reference electrode are aligned in the axial direction.

3. The wrist-worn input device according to claim 1, wherein the one and more electrodes further comprises at least one ground electrode, and
    wherein the at least one ground electrode is located in alignment with the first position determiner along the axial direction.

4. The wrist-worn input device according to claim 1, wherein the first position determiner is a cutout formed in an end edge portion of the band at the first opening.

5. The wrist-worn input device according to claim 1, wherein the first position determiner is a recess formed on the internal surface of the band.

6. The wrist-worn input device according to claim 5, wherein the recess is a through-hole penetrating through the band, and
wherein the first position determiner comprises a cap closing the through-hole on an external surface of the band.

7. The wrist-worn input device according to claim 6, wherein at least part of the cap is transparent.

8. The wrist-worn input device according to claim 6, wherein the cap detachably closes the through-hole.

9. The wrist-worn input device according to claim 1, wherein the band comprises a first band portion and a second band portion lower in flexibility than the first band portion, and
wherein the first position determiner is formed in the first band portion.

10. The wrist-worn input device according to claim 1, further comprising a second position determiner that is located closer to the second opening, and has a shape to be engaged with at least part of the periphery of the styloid process of ulna of the user.

11. The wrist-worn input device according to claim 10, wherein the at least one measurement electrode is located at the center point.

12. The wrist-worn input device according to claim 1, wherein the one or more electrodes further comprise a plurality of reference electrodes,
wherein each of the reference electrodes is used to measure a reference potential that is used to normalize the biopotential measured using the at least one measurement electrode, and
wherein the measurer normalizes the biopotential measured using the at least one measurement electrode by selectively using one of a plurality of reference potentials measured using the reference electrodes.

13. The wrist-worn input device according to claim 1, further comprising on an external surface of the tubular structure a display having a width in a lateral direction and a height in a vertical direction,
wherein the first position determiner is located above a center of the display.

14. The wrist-worn input device according to claim 1, further comprising a display on an external surface of the tubular structure,
wherein the display displays a screen in alignment such that the first position determiner is located above a center of the screen.

15. A wrist-worn input device measuring a biopotential for use in inputting a gesture, comprising:
a band that forms at least part of a tubular structure having a first opening and a second opening at two ends thereof in an axial direction thereof;
one or more electrodes open to an internal surface of the band;
a first position determiner that is located close to the first opening and has a shape to be engaged with at least part of the periphery of the styloid process of ulna of a user;
a sensor that measures the biopotential of the user using the one or more electrodes; and
a communication device that transmits the biopotential of the user measured by the sensor,
wherein the one or more electrodes include at least one measurement electrode, and
wherein the at least one measurement electrodes is located at a center point between the first opening and the second opening along the axial direction or located at a point closer to the second opening than to the center point along the axial direction.

16. A wrist-worn input device, comprising:
a band in a rectangular development shape, except a cutout, extending along a first longitudinal line and a second longitudinal line, and having the cutout extending along the first longitudinal line; and
a plurality of electrodes including one or more measurement electrodes, one or more reference electrodes, and one or more ground electrodes, each of the electrodes open to an internal surface of the band,
wherein a center line extends along the internal surface between the first longitudinal line and the second longitudinal line,
wherein the one or more measurement electrodes are located in an area between the center line and the second longitudinal line,
wherein one or more potentials measured by using the one or more measurement electrodes are normalized by using one or more potentials measured by the one or more reference electrodes,
wherein a longest distance between the cutout and the one or more reference electrodes is shorter than a shortest distance between the cutout and the one or more measurement electrodes, and
wherein the one or more reference electrodes and the one or more ground electrodes are located in an area between a line running from a first intersection of the cutout and the first longitudinal line in perpendicular to the second longitudinal line and a line running from a second intersection of the cutout and the first longitudinal line in perpendicular to the second longitudinal line.

* * * * *